(12) United States Patent
Ellis et al.

(10) Patent No.: US 10,804,562 B2
(45) Date of Patent: Oct. 13, 2020

(54) METHOD AND SYSTEM FOR DETERMINING CONCENTRATION OF ELECTROLYTE COMPONENTS FOR LITHIUM-ION CELLS

(71) Applicant: Tesla Motors Canada ULC, North York (CA)

(72) Inventors: Leah Devorah Ellis, Halifax (CA); Samuel Buteau, Halifax (CA); Samuel Gerard Carson Hames, Halifax (CA); Jeffery R. Dahn, Halifax (CA); David Scott Hall, North York (CA)

(73) Assignee: Tesla Motors Canada ULC, Ontario (CA)

( * ) Notice: Subject to any disclaimer, the term of this patent is extended or adjusted under 35 U.S.C. 154(b) by 264 days.

(21) Appl. No.: 15/833,662

(22) Filed: Dec. 6, 2017

(65) Prior Publication Data
US 2019/0173122 A1    Jun. 6, 2019

(51) Int. Cl.
*G01N 21/31* (2006.01)
*G01N 21/35* (2014.01)
(Continued)

(52) U.S. Cl.
CPC ...... *H01M 10/0525* (2013.01); *C01D 15/005* (2013.01); *G01N 21/314* (2013.01);
(Continued)

(58) Field of Classification Search
CPC ............ H01M 10/0525; H01M 10/484; G01N 21/552; G01N 21/35; G01N 21/314;
(Continued)

(56) References Cited

U.S. PATENT DOCUMENTS

| | | | |
|---|---|---|---|
| 9,281,541 B2 | 3/2016 | Tokuda et al. | |
| 2003/0050541 A1* | 3/2003 | Wuori | A61B 5/14532 600/316 |

(Continued)

OTHER PUBLICATIONS

Wu, W., et al. "Apply machine learning to the design of materials for lithium ion battery" Material Sci. Nanotechnology, 2017; 1(1) pp. 1-12, Sep. 26, 2017.
(Continued)

*Primary Examiner* — Mohammad K Islam
(74) *Attorney, Agent, or Firm* — Knobbe, Martens, Olson & Bear, LLP

(57) ABSTRACT

A computer-implemented method for determining a concentration of a component of an electrolyte in a lithium-ion or for a lithium-ion cell is provided. The method includes providing, to a spectrometer, instructions to capture a spectrum of a sample solution of the electrolyte and generate a signal. The method includes analyzing the signal to determine one or more spectral features of the spectrum. The method includes preparing a database of spectra corresponding to solutions having predetermined concentrations of the component of the electrolyte wherein the database includes a plurality for spectral features for each solution. The method further includes determining a machine learning (ML) model using the database of spectra. The method includes determining the concentration of the component of the electrolyte in the sample solution using the machine learning model.

19 Claims, 12 Drawing Sheets

(51) Int. Cl.
| | |
|---|---|
| H01M 10/0525 | (2010.01) |
| C01D 15/00 | (2006.01) |
| G01N 21/65 | (2006.01) |
| G16C 20/70 | (2019.01) |
| G01N 21/552 | (2014.01) |
| G16C 20/30 | (2019.01) |
| G06F 17/17 | (2006.01) |
| G16C 20/90 | (2019.01) |

(52) U.S. Cl.
CPC ........... *G01N 21/35* (2013.01); *G01N 21/552* (2013.01); *G01N 21/65* (2013.01); *G16C 20/30* (2019.02); *G16C 20/70* (2019.02); *G01N 2021/3155* (2013.01); *G01N 2021/3595* (2013.01); *G06F 17/17* (2013.01); *G16C 20/90* (2019.02)

(58) Field of Classification Search
CPC ........... G01N 21/65; G01N 2021/3595; G01N 2021/3155; G16C 20/30; G16C 20/70; G16C 20/90; C01D 15/005
See application file for complete search history.

(56) References Cited

U.S. PATENT DOCUMENTS

| | | | | |
|---|---|---|---|---|
| 2004/0005717 | A1* | 1/2004 | Soller | A61B 5/14546 436/164 |
| 2004/0046121 | A1* | 3/2004 | Golden | G01J 3/44 250/339.07 |
| 2009/0303462 | A1* | 12/2009 | Munger | A61B 5/0059 356/39 |
| 2010/0173221 | A1* | 7/2010 | Yoshida | H01M 4/90 429/483 |
| 2013/0095392 | A1 | 4/2013 | Shin et al. | |
| 2014/0220428 | A1* | 8/2014 | Zinck | H01M 10/05 429/200 |
| 2014/0295219 | A1 | 10/2014 | Bhat et al. | |
| 2015/0066377 | A1* | 3/2015 | Parchen | G01J 3/44 702/19 |
| 2015/0221977 | A1 | 8/2015 | Hallac et al. | |
| 2015/0260695 | A1* | 9/2015 | Spartz | G01N 30/8606 250/339.01 |
| 2015/0280290 | A1 | 10/2015 | Saha et al. | |
| 2016/0149263 | A1 | 5/2016 | Hallac et al. | |
| 2016/0218394 | A1* | 7/2016 | Yamada | H01M 10/0569 |
| 2016/0233548 | A1* | 8/2016 | Yamada | H01M 10/0525 |
| 2016/0268633 | A1 | 9/2016 | Schofield et al. | |
| 2017/0059411 | A1* | 3/2017 | Pinchuk | G01J 3/45 |
| 2017/0131357 | A1* | 5/2017 | Nieva | H01M 10/48 |
| 2017/0207464 | A1* | 7/2017 | Gyenge | H01M 4/8853 |
| 2018/0316061 | A1* | 11/2018 | Kuroda | H01M 10/0569 |
| 2019/0337807 | A1* | 11/2019 | Xu | C01B 32/215 |

OTHER PUBLICATIONS

Chapman, N., et al., "Spectroscopic and Density Functional Theory Characterization of Common Lithium Salt Solvates in Carbonate Electrolytes for Lithium Batteries", J. Phys. Chem. C 2017, 121, pp. 2135-2148, Jan. 3, 2017.
PCT International Search Report and Written Opinion for related PCT Application No. PCT/CA2018/051371 dated Jan. 16, 2019.
Dell'Anna, et al; Pollen discrimination and classification by Fourier transform infrared (FT-IR) microspectroscopy and machine learning; Anal Bioanal Chem 394; 2009; pp. 1443-1452.
Ellis, et al.; Rapid and Quantitative Detection of the Microbial Spoilage of Meat by Fourier Transform Infrared Spectroscopy and Machine Learning; Applied and Environmental Microbiology; vol. 68, No. 6; Jun. 2002; pp. 2822-2828.
Gachot, et al.; Gas Chromatography/Mass Spectrometry as a Suitable Tool for the Li-Ion Battery Electrolyte Degradation Mechanisms Study; American Chemical Society; Analytical Chemistry; vol. 83, No. 2; Jan. 15, 2011; pp. 478-485; [Published on the web Dec. 14, 2010].
Goodacre, Royston; Explanatory analysis of spectroscopic data using machine learning of simple, interpretable rules; Vibrational Spectroscopy 32; 2003; pp. 33-45.
Gueguen, et al.; Decomposition of LiPF6 in High Energy Lithium-Ion Batteries Studied with Online Electrochemical Mass Spectrometry; Journal of The Electrochemical Society; vol. 163; 2016; pp. A1095-A1100.
Handel, et al.; Thermal aging of electrolytes used in lithium-ion batteries—An investigation of the impact of protic impurities and different housing materials; Journal of Power Sources 267; 2014; pp. 255-259.
Kardamakis, et al.; Linear predictive spectral coding and independent component analysis in identifying gasoline constituents using infrared spectroscopy; ScienceDirect; Chemometrics and Intelligent Laboratory Systems 89; 2007; pp. 51-58.
Kraft, et al.; Qualitative and quantitative investigation of organophosphates in an electrochemically and thermally treated lithium hexafluorophosphate-based lithium ion battery electrolyte by a developed liquid chromatography-tandem quadrupole mass spectrometry method; The Royal Society of Chemistry; vol. 6; 2016; pp. 8-17.
Kraft, et al.; Two-dimensional ion chromatography for the separation of ionic organophosphates generated in thermally decomposed lithium hexafluorophosphate-based lithium ion battery electrolytes; Journal of Chromatography A; vol. 1409; 2015; pp. 201-209.
Monnighoff, et al.; Super critical carbon dioxide extraction of electrolyte from spent lithium ion batteries and its characterization by gas chromatography with chemical ionization; Journal of Power Sources 352; 2017; pp. 56-63.
Nowak, et al.; Review—Chemical Analysis for a Better Understanding of Aging and Degradation Mechanisms of Non-Aqueous Electrolytes for Lithium Ion Batteries: Method Development, Application and Lessons Learned; Journal of the Electrochemical Society; vol. 162; 2015; pp. A2500-A2508.
Petibon, et al; Study of Electrolyte Components in Li Ion Cells Using Liquid-Liquid Extraction and Gas Chromatography Coupled with Mass Spectrometry; Journal of The Electrochemical Society; vol. 161; 2014; pp. A1167-A1172.
Schultz, et al.; Quantitative investigation of the decomposition of organic lithium ion battery electrolytes with LC-MS/MS; Royal Society of Chemistry; RSC Adv.; vol. 7; 2017; pp. 27853-27862.
Schultz, et al.; Separation and Quanitification of Organic Electrolyte Components in Lithium-Ion Batteries via a Developed HPLC Method; Journal of the Electrochemical Society; vol. 162; 2015; pp. A629-A634.
Weber, et al.; Identification of alkylated phosphates by gas chromatography—mass spectrometric investigations with different ionization principles of a thermally aged commercial lithium ion battery electrolyte; Journal of Chromatography; vol. 1394; 2015; pp. 128-136.
Weber; et al; Ion and gas chromatography mass spectrometry investigations of organophosphates in lithium ion battery electrolytes by electrochemical aging at elevated cathode potentials; Journal of Power Sources 306; 2016; pp. 193-199.
Wiemers-Meyer, et al.; Mechanistic insights into lithium ion battery electrolyte degradation—a quantitative NMR study; The Royal Society of Chemistry; Phys. Chem. Chem. Phys; 2016; 18; pp. 26595-26601.
Wilken, et al.; Initial stages of thermal decomposition of LiPF6-based lithium ion battery electrolytes by detailed Raman and NMR spectroscopy; The Royal Society of Chemistry; 2013; pp. 16359-16364.
Wang, et al.; A Systematic Study of Electrolyte Additives in Li[Ni1/3Mn1/3Co1/3]O2 (NMC)/Graphite Pouch Cells; Journal of Electrochemical Society, 161 (12) (2014); Aug. 23, 2014; pp. A1818-A1827.

* cited by examiner

| REGION / CM$^{-1}$ | FEATURE | ASSIGNMENT |
|---|---|---|
| [EC]: | | |
| 1) 780 ± 25 | CENTER | CO$_3$ NON-PLANAR ROCK |
| 2) 1170 ± 40 | AREA | CO$_2$ SYMMETRIC STRETCH (EC) |
| 3) 1270 ± 30 | CENTER | CO$_2$ SYMMETRIC STRETCH (DMC) |
| 4) 1290 ± 75 | CENTER | CO$_2$ SYMMETRIC STRETCH (DMC) |
| 5) 1443 ± 60 | CENTER | C-O ASYMMETRIC STRETCH |
| 6) 1710 ± 20 | AREA | C=O, STRETCH |
| 7) 1775 ± 80 | AREA | C=O, STRETCH |
| 8) 1775 ± 60 | CENTER | C=O, STRETCH |
| [LiPF$_6$]: | | |
| 9) 780 ± 25 | AREA | CO$_3$ NON-PLANAR ROCK |
| 10) 839 ± 25 | AREA | LiPF$_6$ t$_{1u}$ |
| 11) 1290 ± 75 | CENTER | CO$_2$ SYMMETRIC STRETCH (DMC) |
| 12) 1320 ± 30 | CENTER | CO$_2$ SYMMETRIC STRETCH |

FIG. 5

| METHOD | ANALYTES | APPROXIMATE ACCURACY | PREPARATION | SPEED | INSTRUMENT COST |
|---|---|---|---|---|---|
| FTIR-ML | ORGANIC SOLVENTS $LiPF_6$ | 3-5 WT. % 5 % IN MOLARITY | NONE | ~1m / SAMPLE | ~$18,000 USD |
| GC-MS | ORGANIC SOLVENTS ELECTROLYTE ADDITIVES TRACE COMPONENTS | 1-2 WT. % | Extraction, $CH_2Cl_2$ | ~1h / SAMPLE | ~$100,000 USD |
| ICP-OES | $LiPF_6$ | 3-5 WT. % | DILUTION, $HNO_3$ | ~1h / SAMPLE | ~$100,000 USD |
| NMR | ORGANIC SOLVENTS Li SALTS ELECTROLYTE ADDITIVES TRACE COMPONENTS | HARD TO MAKE FULLY QUANTITATIVE | DILUTION, DEUTERATED SOLVENT | ~30 MIN / SAMPLE | >$100,000 USD |

FIG. 9

| ELECTROLYTE | METHOD | LiPF$_6$ / wt. % | EC / wt. % | DMC / wt. % |
|---|---|---|---|---|
| FRESH | AS PREPARED | 14.5 | 25.6 | 59.8 |
| | GC-MS/ICP-OES | 13.1 ± 0.1 | 26.5 ± 0.2 | 60.4 ± 0.3 |
| | FTIR-ML | 13.3 ± 0.4 | 27.5 ± 1.5 | 59.3 ± 1.2 |
| 4.1 V | GC-MS/ICP-OES | 9.8 ± 0.2 | 29.51 ± 0.03 | 60.7 ± 0.2 |
| | FTIR-ML | 10.08 ± 0.02 | 25.35 ± 0.04 | 64.57 ± 0.03 |
| 4.3 V | GC-MS/ICP-OES | 12.5 ± 0.2 | 29.8 ± 0.1 | 57.8 ± 0.1 |
| | FTIR-ML | 11.4 ± 0.4 | 25.4 ± 1.1 | 63.2 ± 0.9 |
| 4.5 V | GC-MS/ICP-OES | 11.8 ± 0.1 | 30.22 ± 0.03 | 58 ± 0.3 |
| | FTIR-ML | 10.5 ± 0.6 | 26.3 ± 0.6 | 63.3 ± 0.5 |

*FIG. 11*

MINOR COMPONENTS FOUND BY GC-MS IN AGED ELECTROLYTE

| CELL TYPE | EMC (% wt.) | FEC (% wt.) | DMOHC (% wt.) |
|---|---|---|---|
| 4.1 V | 0 ± 0 | 0.6 ± 0.01 | 0.471 ± 0.001 |
| 4.3 V | 0.1 ± 0.1 | 0.73 ± 0.02 | 0.3 ± 0.3 |
| 4.5 V | 0.29 ± 0.02 | 0.77 ± .02 | 0.3 ± 0.3 |

*FIG. 12*

METHOD AND SYSTEM FOR DETERMINING CONCENTRATION OF ELECTROLYTE COMPONENTS FOR LITHIUM-ION CELLS

TECHNICAL FIELD

The present disclosure relates to characterizing the electrolyte within lithium-ion cells. More particularly, the present disclosure relates to methods and systems for determining concentration of electrolyte components for lithium-ion cells using advanced techniques to analyze experimental data from a spectrometer.

BACKGROUND

A major cause of failure in lithium-ion batteries or cells, especially in high voltage cells, is the degradation of the electrolyte, particularly at the surface of the charged electrodes. Existing solutions to address cell failure and electrolyte degradation are focused on the films of electrolyte decomposition products which build up on the surfaces of the electrodes. These films contain chemical moieties derived from both the electrolyte solvents and the electrolyte salt, such as, lithium hexafluorophosphate ($LiPF_6$). For example, $LiPF_6$ decomposes into $LiF$ and $PF_5$, and the latter readily hydrolyzes to form $HF$ and $PF_3O$. These two hydrolysis products are highly reactive on both the electrodes, and their unavoidable presence in $LiPF_6$ solutions may have a detrimental impact on the electrodes' performance. Although mechanisms for the consumption of the electrolyte solvents and the electrolyte salt $LiPF_6$ in lithium-ion cells have been determined, there does not exist an inexpensive and accurate way to characterize an unknown electrolyte and thus determine the extent to which the electrolyte has degraded.

Typically, quantitative analyses of electrolyte solutions focus on expensive analytical tools, such as nuclear magnetic resonance (NMR) spectrometers, gas chromatograph-mass spectrometers (GC-MS), high-performance liquid chromatography (HPLC) instruments, and inductively coupled plasma optical emission spectrometers (ICP-OES), and require significant time to perform the analysis. Further, some analytical tools cannot even measure the concentration of electrolyte components directly. For example, the columns or detectors used in chromatography-based methods cannot be exposed to the high temperature decomposition products of $LiPF_6$, so these methods focus only on the organic portions of the electrolyte, after the water-soluble portions of the electrolyte have been removed.

Hence, there is a need for methods and systems for characterizing the electrolyte in a lithium-ion cell that overcomes the aforementioned drawbacks.

SUMMARY

The present disclosure provides a computer-implemented method for determining a concentration of a component of an electrolyte in a lithium-ion cell. The computer-implemented method includes providing, to a spectrometer, instructions to capture a spectrum of a sample solution of the electrolyte and generate a signal. The method includes receiving the signal from the spectrometer. The method includes analyzing the signal to determine one or more spectral features of the spectrum. The method includes preparing a database of spectra corresponding to solutions having predetermined concentrations of the component of the electrolyte wherein the database includes a plurality for spectral features for each solution. The method further includes determining a machine learning (ML) model using the database of spectra, wherein the machine learning model is based on at least one of the plurality of spectral features and the concentration of the component of the electrolyte. Subsequently, the method includes determining the concentration of the component of the electrolyte in the sample solution using the machine learning model.

In certain embodiments, a system for determining the concentration of the component of the electrolyte in the lithium-ion cell is provided. The system includes the spectrometer configured to subject the sample solution of the electrolyte to electromagnetic radiation and to capture the spectrum of the sample solution of the electrolyte. The spectrometer is configured to produce the signal representing the spectrum. The system includes a processor in electrical communication with the spectrometer. The processor is configured to analyze the signal to determine one or more spectral features of the spectrum. The processor is configured to prepare the database of spectra corresponding to solutions having predetermined concentrations of the component of the electrolyte, wherein the database includes a plurality for spectral features for each solution. The processor determines the machine learning model using the database of spectra, wherein the machine learning model is based on at least one of the plurality of spectral features and the concentration of the component of the electrolyte. The processor is configured to determine the concentration of the component of the electrolyte in the sample solution using the machine learning model.

In certain embodiments of the invention, a computer-program product for use in conjunction with a spectrometer to determine a concentration of a component of an electrolyte in a lithium-ion cell is provided. The computer-program product includes a non-transitory computer-readable storage medium having instructions that are executed by a processor. The processor is configured to analyze the signal to determine one or more spectral features of the spectrum. The processor is configured to prepare a database of spectra corresponding to solutions having predetermined concentrations of the component of the electrolyte, wherein the database includes a plurality for spectral features for each solution. The processor determines a machine learning model using the database of spectra, wherein the machine learning model is based on at least one of the plurality of spectral features and the concentration of the component of the electrolyte. The processor is configured to determine the concentration of the component of the electrolyte in the sample solution using the machine learning model.

BRIEF DESCRIPTION OF THE FIGURES

FIG. 5 is a table listing FTIR regions, features and vibrational modes used as part of the analysis to determine concentrations of ethylene carbonate (EC) and $LiPF_6$ according to certain embodiments of the invention.

FIG. 9 is a table showing comparison of common methods employed for the characterization of electrolyte solutions according to certain embodiments of the invention.

FIG. 11 is a table listing major components (weight %) of the fresh electrolyte and the electrolyte from the cells cycled at 55° C., obtained by GC/MS, ICP-OES and FTIR/ML methods according to certain embodiments of the invention.

FIG. 12 is a table listing minor constituents found by GC/MS in the electrolytes of the tested cells according to certain embodiments of the invention.

Figure 1:
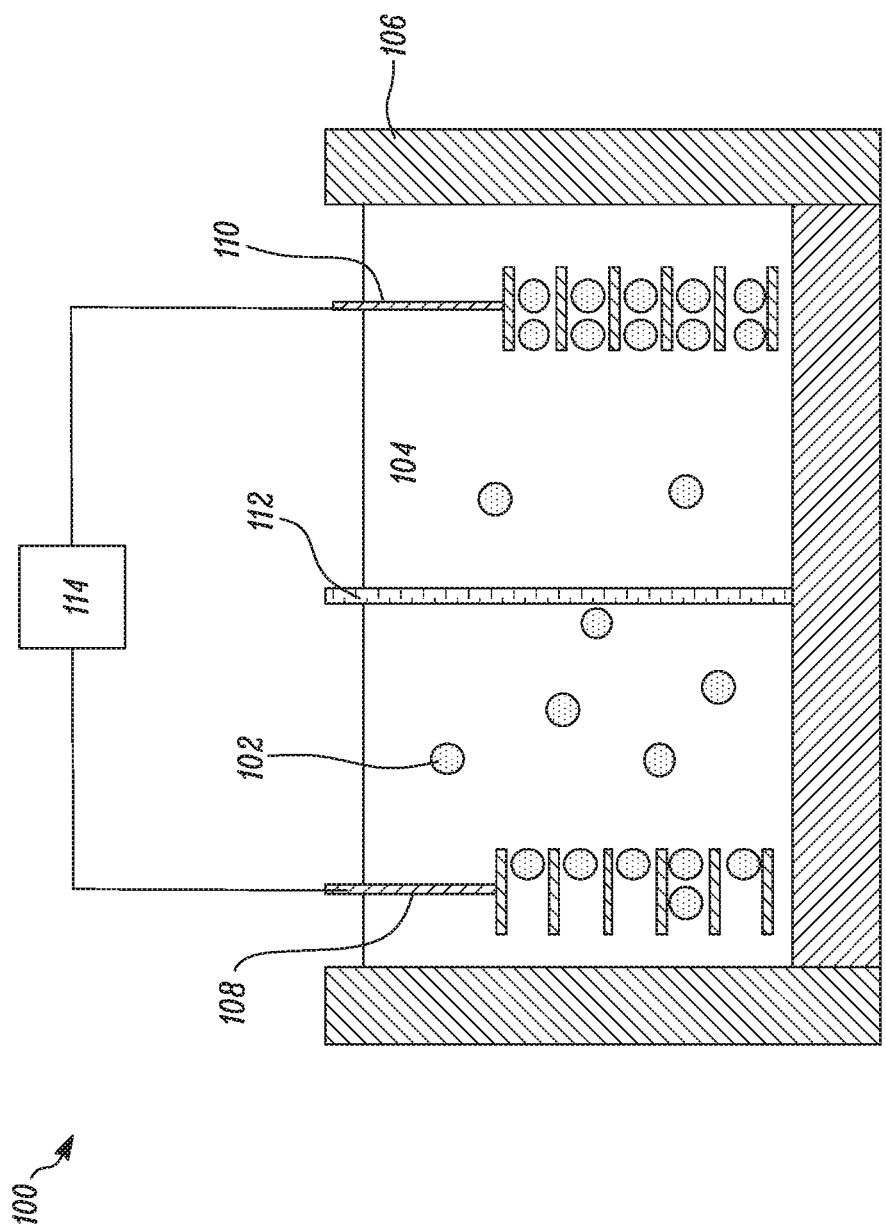
FIG. 1 is a schematic diagram of a lithium-ion, battery-cell system.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting it.

DETAILED DESCRIPTION

Lithium-ion batteries and cells used in high-voltage applications such as, in automobiles and energy storage, are becoming increasingly prevalent. FIG. 1 illustrates a schematic of a lithium-ion cell 100. Lithium-ions 102 are dispersed throughout an electrolyte 104, within a container 106. Container 106 may be part of a battery cell. The lithium-ions 102 migrate between a positive electrode 108 and a negative electrode 110. A separator 112 separates the negative electrode 110 and the positive electrode 108. Circuitry 114 connects the negative electrode 110 and the positive electrode 108. A major cause of failure in lithium-ion batteries or cells, especially in the high-voltage applications in automobiles and energy storage, is the degradation of the electrolyte, particularly at the surface of the charged electrodes. To quickly study the impact of usage on the electrolyte, rapid and accurate techniques like those described herein are needed.

Figure 2:
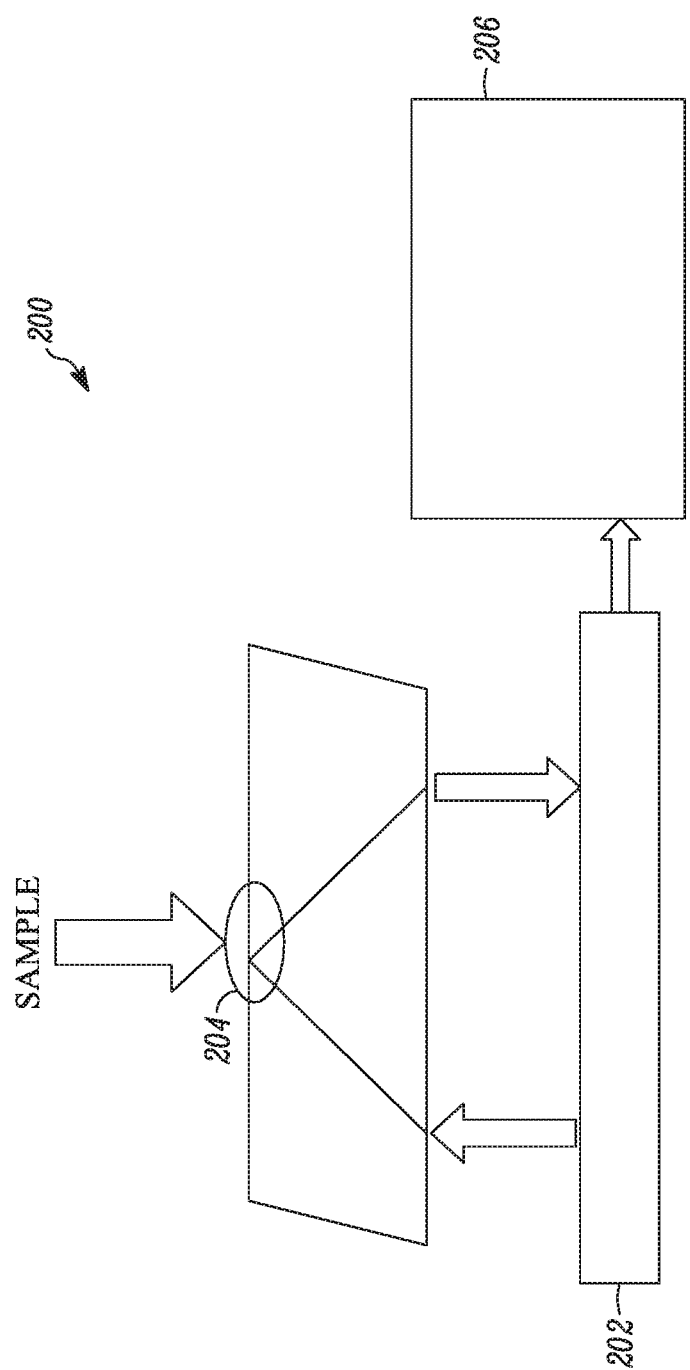
FIG. 2 illustrates a system for determining a concentration of an electrolyte component in an electrolyte sample according to certain embodiments of the invention.

FIG. 2 illustrates an exemplary system 200 for characterizing the electrolyte concentration according to certain embodiments of the present invention. In this embodiment, system 200 is a stand-alone spectrometer 202. The spectrometer 202 is configured to generate electromagnetic radiation to be passed through the electrolyte sample. The spectrometer 202 may be an infrared spectrometer, a Raman spectrometer, an ultraviolet visible (UV-Vis) spectrometer, an HPLC, or a Fourier transform infrared (FTIR) spectrometer. System 200 may include an attenuated total reflection (ATR) substrate 204 such as, for example, a germanium crystal for receiving the electrolyte sample. An electromagnetic beam is generated by the spectrometer 202 and may be imposed on the electrolyte sample provided on ATR substrate 204. The electrolyte sample may be provided directly on the spectrometer 202. The spectrometer 202 is configured to detect the radiation received from the electrolyte sample and produce a signal representing the spectrum. The signal represents one or more characteristics such as, but not limited to, transmittance or absorbance, of the electrolyte sample.

The signal is passed on to a processor 206, electrically connected with spectrometer 202, for further processing. Processor 206 may be implemented as a part of a computer system described later. Processor 206 is configured to use machine learning (ML) algorithms to determine the concentration of the electrolyte components in the lithium-ion cell. In certain embodiments, processor 206 is part of the spectrometer 202.

Processor 206 is configured to prepare a database of spectra obtained from analysis of electrolyte samples of known concentrations. In case FTIR spectrometer 202 is used, the database of FTIR spectra is prepared. The database of FTIR spectra is used to train a machine learning model. In certain embodiments, one or more spectral features of the absorbance FTIR spectra may be measured. For example, a spectral feature may include an area of the signal in a region centered around 839 $cm^{-1}$ and with a half width of 25 $cm^{-1}$. The variation of each feature with the concentration of the component of the electrolyte may be fitted to a surface defined by a polynomial function. The fitting may be performed using a least squares fitting technique. Once all the surfaces are known, processor 206 is configured to perform fitting of the spectral features of the FTIR spectrum of the unknown sample to the surfaces determined using the machine learning model and determine the values of the concentrations of the components of the electrolyte giving the best fit. Although certain embodiments of this invention have been described using infrared spectrum obtained using FTIR spectrometer, it would be obvious to a person skilled in the art that various spectrometers known in the art may be used without departing from the spirit and the scope of the invention.

Figure 3:
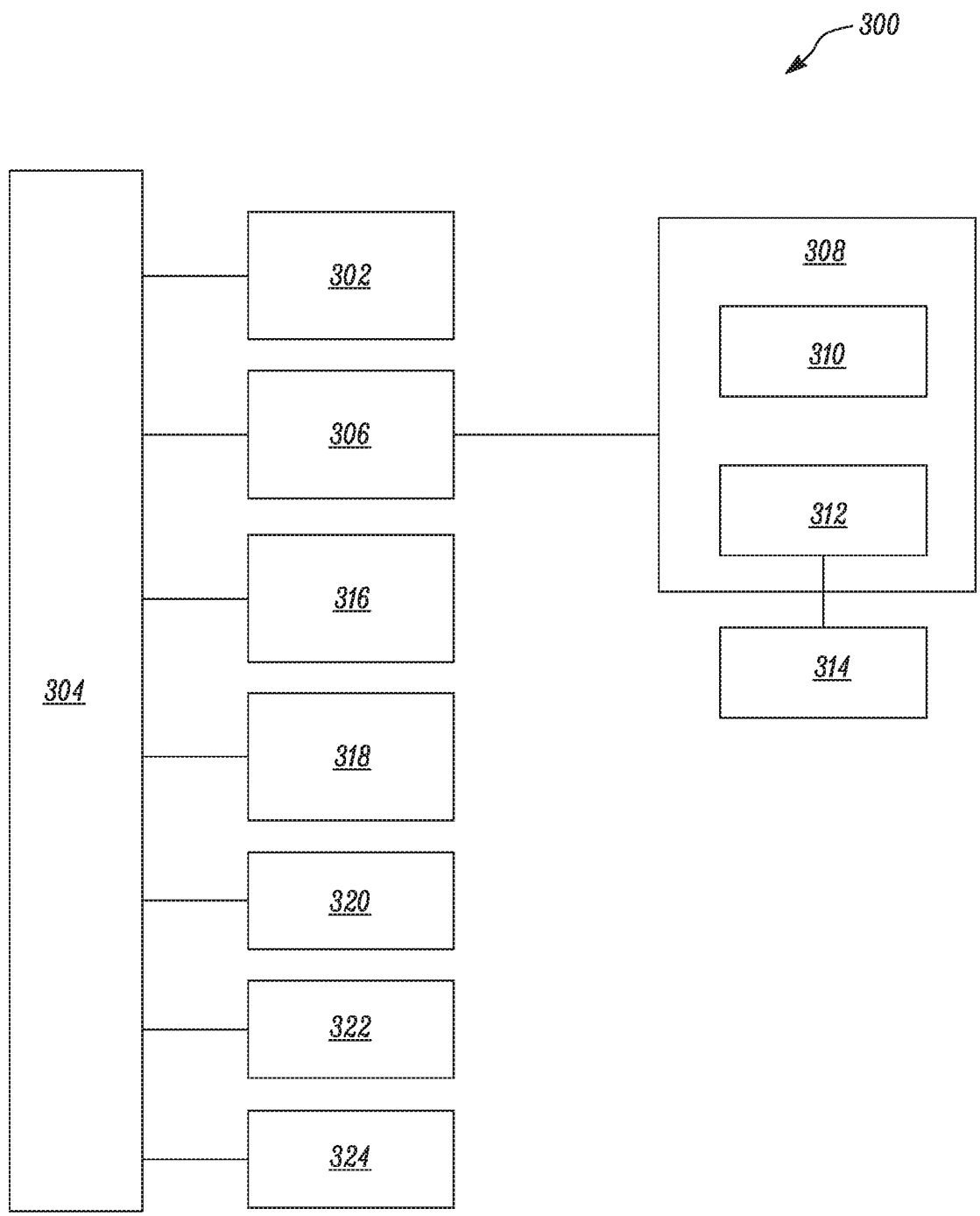
FIG. 3 illustrates an exemplary computer system for characterizing the concentration of the electrolyte component in a lithium-ion cell according to certain embodiments of the invention.

FIG. 3 illustrates an exemplary computer system 300 according to certain embodiments of the invention. Specifically, FIG. 3 illustrates the computer system 300 that can include, e.g., a personal computer (PC) system running an operating system such as, e.g., Windows NT/98/2000/CE, OS/2, Mac/OS, LINUX, or other variants of the UNIX operating system. However, the invention is not limited to these platforms. Instead, the invention can be implemented on any appropriate computer system running any appropriate operating system, such as Solaris, Irix, Linux, HPUX, OSF, Windows 98, Windows NT, OS/2, and Mac/OS.

Computer system 300 includes one or more processors, such as processor 302. The functionality of processor 302 is similar to processor 206 discussed earlier. The processor 302 is connected to a communication bus 304. The computer system 300 may also include a main memory 306, preferably random access memory (RAM), and a secondary memory 308. The secondary memory 308 may include, e.g., a hard disk drive 310, or storage area network (SAN) and/or a removable storage drive 312, representing a floppy diskette drive, a magnetic tape drive, a compact disk drive, etc. Removable storage drive 312 reads from and/or writes to a removable storage unit 314.

Removable storage unit 314, also called a program storage device or a computer program product, represents a floppy disk, magnetic tape, compact disk, etc. The removable storage unit 314 includes a computer usable storage medium having stored therein computer software and/or data.

The computer system 300 also includes an input device such as, but not limited to, a mouse 316 or other pointing device such as a digitizer, and a keyboard 318 or other data entry device. The computer system 300 may also include output devices, such as, e.g., display 320. The computer system 300 may include input/output (I/O) devices such as, e.g., network interface cards 322 and modem 324.

Computer programs (also called computer control logic), including object oriented computer programs and instructions, are stored in main memory 306 and/or the secondary memory 308 and/or removable storage units 314, also called computer program products. Such computer programs, when executed, enable computer system 300 to perform the features of the present invention as discussed herein. In particular, the computer programs, when executed, enable the processor 302 to perform the features of the present invention. Accordingly, such computer programs represent controllers of the computer system 300.

Figure 4:
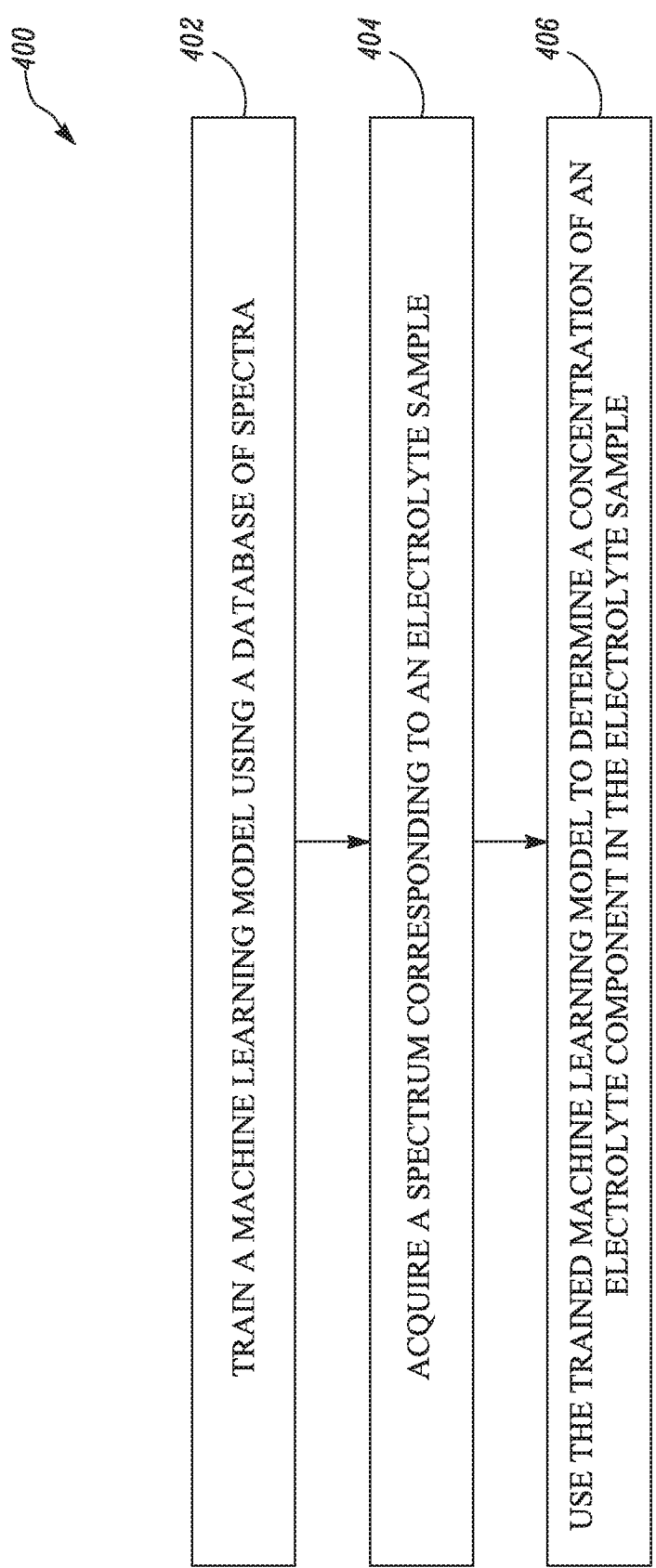
FIG. 4 illustrates a method for characterizing the concentration of the electrolyte component in a lithium-ion cell according to certain embodiments of the invention.

FIG. 4 illustrates a method 400 for characterizing the electrolyte concentration of a lithium-ion cell according to certain embodiments of the present invention. At step 402, the method includes training a machine learning model for determining the concentration of components of the electrolyte. To train the machine learning model, a database of spectra obtained from FTIR analysis of electrolyte samples of known concentrations is prepared. For each spectrum in the database, values or intensities of a plurality of spectral features are measured. For example, a spectral feature may include an area of the signal or a weighted central wavenumber in a region centered around 839 $cm^{-1}$ and with a half width of 25 $cm^{-1}$. The variation of each of the plurality of spectral features with the corresponding concentrations of the components of the electrolyte may be fitted to a surface, for example a surface defined by a polynomial. For each spectral feature, a surface may be obtained using the least squares fitting technique. In certain embodiments, a set of spectral features may be selected out of the plurality of spectral features for training the machine learning model. The set of spectral features may be selected based on a slope of the surface with the concentration of the components. For example, a spectral feature yielding the highest slope of the surface may be selected over a feature yielding the lowest slope.

At step 404, the method includes acquiring infrared spectrum of the sample solution of the electrolyte. Infrared spectrometer 202 is configured to acquire the infrared spectrum and produce a signal. The signal is processed by processor 206 at step 406 to determine the concentration of the components of the electrolyte using the trained machine learning model. Specifically, the method includes fitting the spectral features of the sample solution to the corresponding surface determined by the machine learning model and determining the values of the concentration of the components of the electrolyte giving the best fit.

The present invention is hereinafter further described by way of the following non-limiting examples and accompanying figures.

Example 1

Stock solutions of 7:3 weight ratio ethylene carbonate (EC):dimethyl carbonate (DMC), 2.00 mol/kg $LiPF_6$ in 7:3 weight ratio EC:DMC, and 2.00 mol/kg $LiPF_6$ in DMC were used. Electrolyte samples were prepared in an argon-filled glovebox by mixing the appropriate amounts of $LiPF_6$ (BASF, 99.94%, water content <14 ppm), EC (BASF, 99.46%, water content <3 ppm), and DMC (BASF, >99.99%, water content <10 ppm). These solutions were mixed to form a 9×9 solution matrix of varying ratios of $LiPF_6$, EC, and DMC. All of these 81 electrolyte samples were prepared by serial volume dilutions from the stock solutions, using a 200 μL-2 mL pipette (Rainin pipet-lite XLS). EC and DMC concentrations were then assessed in volume ratios, and $LiPF_6$ in mol/L, as the serial volume dilutions ensured a constant stepwise increase in these units.

To illustrate the effectiveness of the present invention, a set of five known solutions were prepared to test the accuracy and precision of the system 100. The known solutions also contained small amounts of electrolyte additives such as vinylene carbonate (BASF, 99.97%, water content <100 ppm), 1,3-propene sultone (Lianchuang Medicinal Chemistry Co., Ltd., China, 98.20%), and fluoroethylene carbonate (BASF, 99.94%). Electrolyte used in the lithium-ion pouch cells (discussed later in example 2) was also prepared in a similar way and contained 1.2 M $LiPF_6$ in 3:7 weight ratio EC:DMC, with 2% fluoroethylene carbonate (FEC) and 1% 1,3,2-dioxathiolane-2,2-dioxide (DTD) (Suzhou Yacoo Chemical Reagent Co., >98%).

The electrolyte samples were subjected to FTIR spectroscopy. FTIR spectra were collected using a Cary 630 FTIR of Agilent Technologies, equipped with a germanium crystal ATR substrate. The collected spectra corresponding to 81 electrolyte samples were organized to form a database of FTIR spectra. Sixteen scans were collected for each electrolyte sample, at a resolution of 4 $cm^{-1}$, using MicroLab PC software of Agilent Technologies. Fourier transforms were performed using HappGenzel apodization, Mertz phase correction, and a zero-fill factor of 2. All measurements were performed in a thermostatic room (Coldmatic Refrigeration) maintained at 12-14° C. to hinder evaporation of DMC.

The database of FTIR spectra was then processed using a machine-learning algorithm. The analysis range in this example is 650-2000 $cm^{-1}$. In certain embodiments, the spectral region analyzed is the range of 500-1500 $cm^{-1}$ which is often referred to as the "fingerprint region," but which typically is difficult to analyze using conventional techniques. In other embodiments, the analysis region is the range of 500-4000 $cm^{-1}$, which includes the fingerprint region and vibrational excitation energies for various covalently-bonded functional groups. First, the raw FTIR spectra were normalized such that the total integrated area over the analysis range, here 650-2000 $cm^{-1}$, equaled one. Then, 'n' selected spectral features in the absorbance FTIR spectrum of each of the 81 electrolyte samples were measured. FIG. 5 shows an exemplary listing of 12 selected spectral features. Spectral features include area of the signal in a first set of regions and wavenumber of the signal in a second set of regions. Some of the regions out of the first set of regions and the second set of regions may overlap with each other. For example, a spectral feature includes the area of the normalized signal in a region centered around 839 $cm^{-1}$ and with a half width of 25 cm$^{-1}$. Another example of spectral feature includes a weighted central wavenumber within a region centered around 1270 cm$^{-1}$ and with a half width of 30 cm$^{-1}$. This procedure produces an n-component array of values, where each n-component array is associated with an electrolyte sample of known composition.

The values corresponding to each of the 'n' spectral features in the FTIR spectra vary smoothly with composition in the 81 electrolyte samples. The variation of each spectral feature with composition can be fitted to a surface of the form:

$$F_n(x,y)=a_n+b_nx+c_ny+d_nxy+e_nx^2+f_ny^2 \quad [1]$$

where $F_n$ is the value (area or weighted central wavenumber) of the n$^{th}$ spectral feature, x is the LiPF$_6$ concentration, and y is the volume % ratio of EC in the EC/DMC solution. The parameters $a_n$, $b_n$, $c_n$, $d_n$, $e_n$, and $f_n$ are adjustable parameters and the index 'n' covers all the spectral features considered. The parameters are adjusted by least squares fitting to the areas or weighted central wavenumbers of the 81 database samples. A larger or smaller number of spectral features may be considered as desired.

The spectral features selected from the FTIR spectra were determined by trial and visualization. The feature values for the 81 electrolyte samples were plotted together with the fitted surface to determine which spectral features yielded a large slope with composition and good agreement between the measurements and the fit. Many suitable features were found, and the best 12 features were selected as shown in FIG. 5. Then, these 12 features were rescaled to weigh their contribution according to their signal-to-noise ratio. In certain embodiments, the spectral features are determined using the machine learning algorithm given the training spectra and the desired analysis range (for example the entire spectra or a specific portion like the fingerprint region), and then generating a predictive model. The predictive model uses one or multiple features to identify the concentration of the analyte.

To determine the LiPF$_6$ concentration and EC/DMC ratio of an unknown electrolyte sample, the FTIR spectrum of the unknown electrolyte sample was first measured. Then the intensities or central wavenumbers of the 12 selected spectral features were determined. Least squares fitting to the 12 surfaces described by equation 1 was performed to determine which values of x and y gave the best fit. Thus, the LiPF$_6$ concentration and EC/DMC ratio of the unknown electrolyte sample could be determined.

Figure 6:
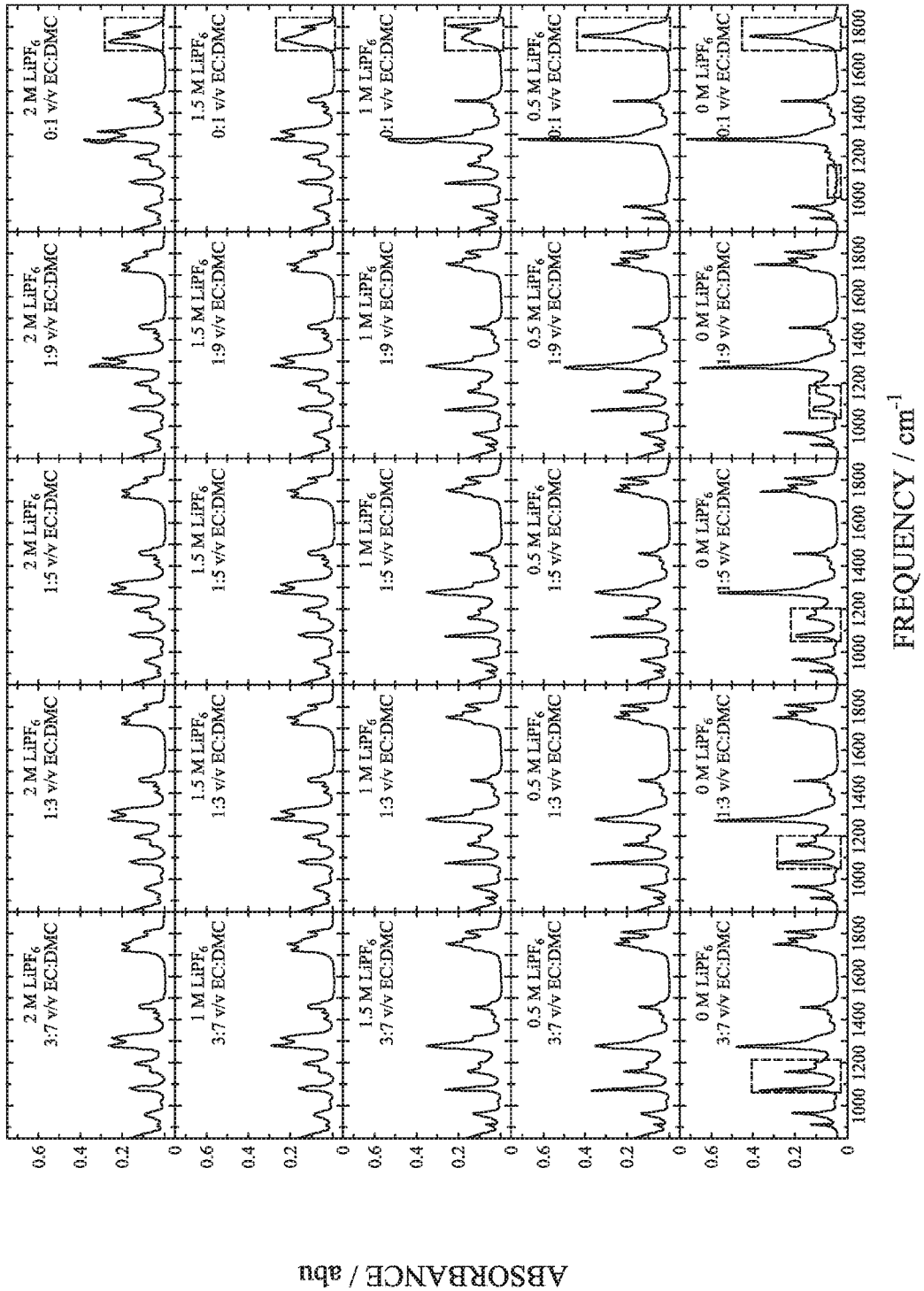
FIG. 6 illustrates FTIR spectra of electrolyte solutions within common ranges of $LiPF_6$, EC, and dimethyl carbonate (DMC) concentrations according to certain embodiments of the invention.

FIG. 6 illustrates FTIR spectra of electrolyte solutions with various concentrations of LiPF$_6$, EC, and DMC. The bottom-right corner shows the spectrum of pure DMC. As the amount of LiPF$_6$ in DMC increases, certain features in the FTIR spectra evolve, in proportion to the amount of LiPF$_6$. The most prominent and well-known of these changes is to the carbonyl, C=O, stretching peak, at around 1750 cm$^{-1}$. The carbonyl peak splits up as the concentration of LiPF$_6$ increases. This is a result of the coordination of the carbonyl group of the solvent molecules to the Li$^+$ of the dissociated LiPF$_6$. The absorbance of this split peak (shown by dotted lines) grows with increasing LiPF$_6$ concentration as one moves from bottom-right corner to top-right corner in FIG. 6. This carbonyl peak can be one of the spectral features used by the machine learning algorithm to determine the concentration of LiPF$_6$ in a solution of organic carbonates. In a similar way, the machine learning algorithm determines the concentration of EC and DMC from the presence of spectral features that vary with the solvent ratio. For EC, the spectral features include the peaks between 1050-1200 cm$^{-1}$ that grow with increasing EC content, and which are caused by the twisting of the adjacent CH$_2$ groups in EC. The presence of DMC can be determined from the strong absorption at 1290 cm$^{-1}$, corresponding to the carbonyl symmetric stretching. This can be clearly distinguished from carbonyl symmetric stretching of EC, which occurs at a much lower wavenumber, 1170 cm$^{-1}$.

In other embodiments, the machine learning algorithm analyzes features related to other functional groups to determine analyte concentration of other systems. In an embodiment, that has an alcohol in the system, the machine learning algorithm uses a feature that corresponds to a characteristic absorbance of the alcohol, such as the O—H stretch, which is a broad singlet located around 3200-1550 cm$^{-1}$. In another embodiment that has a carboxylic acid in the system, the machine learning algorithm determines the concentration of a carboxylic acid using a feature of the carboxylic acid, for example, the C=O stretch, which is a singlet located at 1780-1710 cm$^{-1}$. Alternatively, the machine learning algorithm uses the O—H stretch feature of a carboxylic acid that may appears at 3000-2500 cm$^{-1}$.

Figures 7A, 7B, 7C:
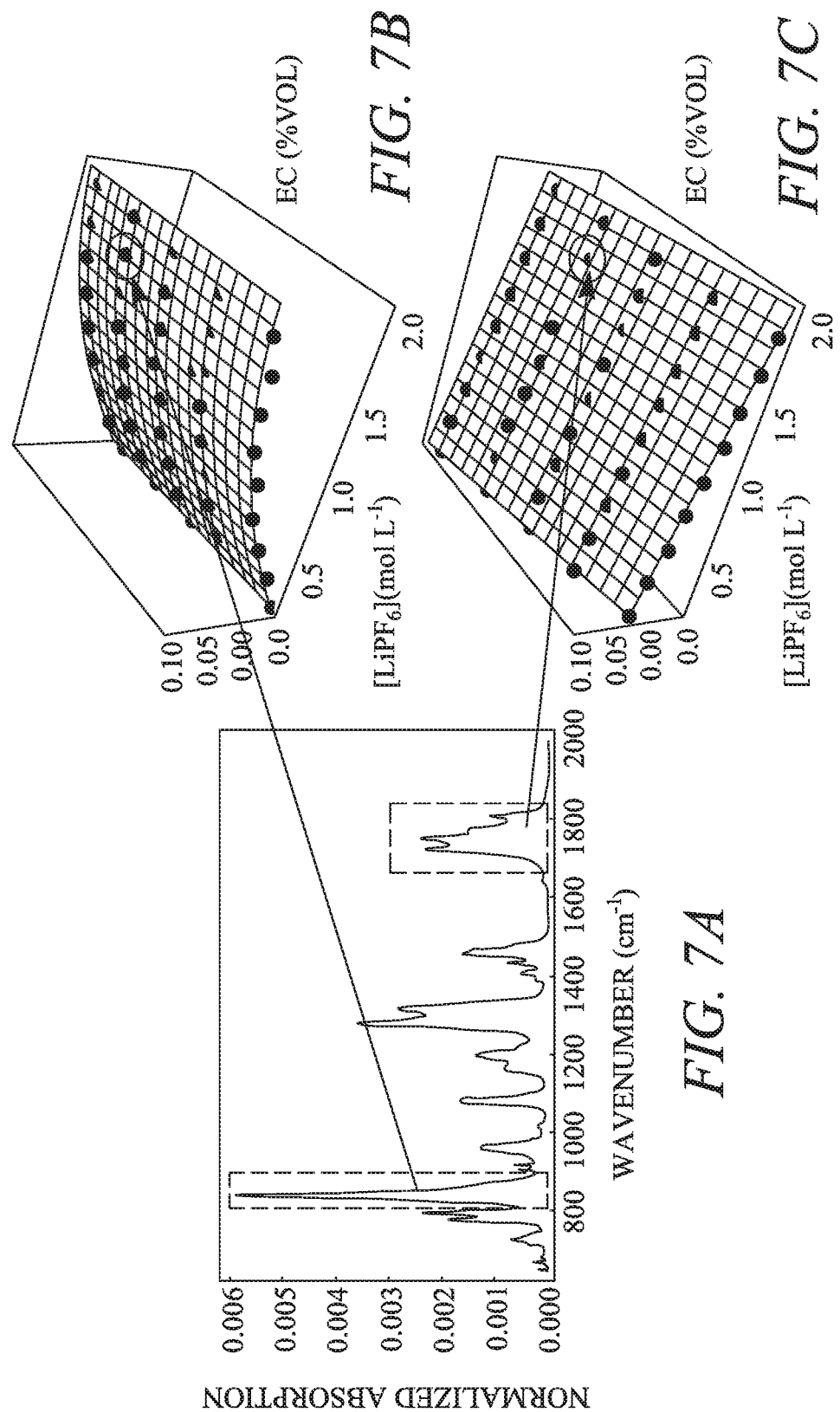
FIG. 7A illustrates a FTIR spectrum of an electrolyte solution composed of 1.75 M $LiPF_6$, 25% (vol) EC in DMC according to certain embodiments of the invention.
FIG. 7B illustrates the variation of the spectral features around 839 $cm^{-1}$ over a range of electrolyte compositions according to certain embodiments of the invention.
FIG. 7C illustrates the variation of the spectral features around 1775 $cm^{-1}$ over a range of electrolyte compositions according to certain embodiments of the invention.

FIG. 7 illustrates the operation of the machine learning algorithm. FIG. 7A shows a representative FTIR spectrum of an electrolyte sample in the range of approximately 650-2000 cm$^{-1}$. In certain embodiments, the spectral region analyzed is the range of 500-1500 cm$^{-1}$ which is often referred to as the "fingerprint region," but which typically is difficult to analyze using conventional techniques. In other embodiments, the analysis region is the range of 500-4000 cm$^{-1}$ which includes the fingerprint region and vibrational excitation energies for various covalently-bonded functional groups. The FTIR spectrum shown in FIG. 7A has been normalized such that the total integrated area over the range 650-2000 cm$^{-1}$ is equal to one. To characterize the electrolyte sample, the features of FTIR spectrum are analyzed by the machine learning algorithm. In this example, twelve regions and features were used to determine the concentration of LiPF$_6$ and the weight fraction of the solvents. These twelve regions and features are illustrated in FIG. 5. FIG. 7A illustrates a FTIR spectrum of an electrolyte solution composed of 1.75 M LiPF$_6$, 25% (vol) EC in DMC with specific features at 839±25 cm$^{-1}$ and 1775±80 cm$^{-1}$ respectively. FIGS. 7B and 7C, show the integrated area of the features over a range of solution compositions, respectively. In FIG. 7B. the feature is an LiPF$_6$-determining feature because the slope of the surface with LiPF$_6$ concentration is large in that surface. In contrast, the feature in FIG. 7C can be used to determine both EC and LiPF$_6$ content since the surface in FIG. 7C slopes strongly in both EC and LiPF$_6$ content. However, all 12 features are used by the machine learning algorithm for the determination of both the solvent ratio and the LiPF$_6$ concentration. The black dots in FIGS. 7B and 7C mark measurements of the database samples used to create the model (the FTIR spectra of some of these solutions were shown in FIG. 6). The surfaces in FIGS. 7B and 7C were fitted from the measured points using a function (equation 1) that is quadratic in both EC vol % and LiPF$_6$ concentration. The arrows in FIGS. 7B and C show the position of the FTIR features from FIG. 7A. For solutions of unknown composition, the position of FTIR features on all 12 surfaces can be used to determine the concentration of the components, if the components are within the model.

Machine learning used in certain embodiments of the invention employs a "supervised", feature-based model. Specific regions in the FTIR spectrum are selected for analysis. The regions selected are those that are most sensitive to the changes in analyte concentrations. This allows a simple model to be built for every region of interest, which reduces the number of parameters in the fit, and therefore reduces the number of spectra needed to train the model. This advantage is significant, since preparation and measurement of high quality samples to build the database is time consuming.

Surfaces, as in FIGS. 7B and 7C, were fitted to the intensity of the 12 spectral features (shown in FIG. 5) as a function of $LiPF_6$ concentration and solvent ratio. In certain embodiments, the quadratic equations of the 12 surfaces then train the model. The FTIR spectrum of an unknown electrolyte sample is then measured and the intensities of the 12 spectral features in the spectrum of the unknown electrolyte sample are calculated. Least-squares fitting was used to determine the best choice of the $LiPF_6$ concentration and solvent ratio that match the 12 measured and database spectral feature intensities.

Figure 8:
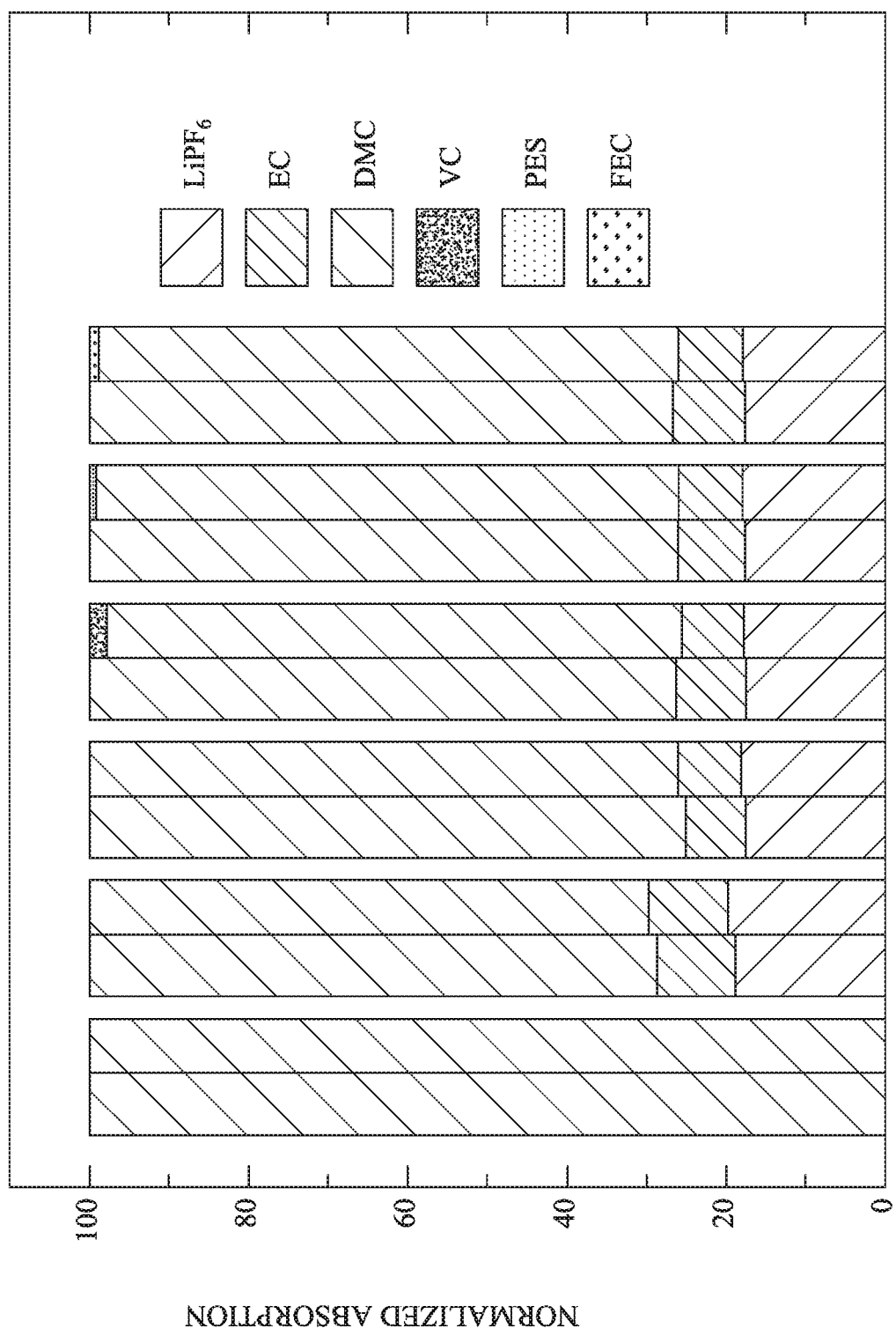
FIG. 8 illustrates the composition of five exemplary solutions that were characterized in an FTIR/ML analysis compared to their known compositions according to certain embodiments of the invention.

FIG. 8 shows the results of an experiment in which the composition of five unknown solutions were characterized according to certain embodiments of the invention. These five solutions were prepared and characterized by different people, so that their compositions remained unknown at the time of analysis. The first solution was pure DMC. The other four solutions contained DMC, $LiPF_6$, EC and optionally, small amounts of common electrolyte additives. The proportions of the electrolyte additives and electrolyte components were chosen to be representative of typical electrolytes that could be used in lithium-ion cells. FIG. 8 shows experimental data that the machine learning algorithm determined the relative ratios of $LiPF_6$, EC and DMC in the electrolyte solutions with accuracy and precision, despite the presence of small amounts of electrolyte additives which were not included in the algorithm's training matrix.

Example 2

In this example, the concentrations of $LiPF_6$ and other electrolyte components were determined using gas chromatography mass spectrometry (GC-MS) technique and inductively coupled plasma atomic emission spectroscopy (ICP-OES) technique and the results were compared with those obtained from machine learning based analysis of FTIR spectra. For this example, machine-made lithium-ion pouch cells, containing $Li[Ni_{0.5}Mn_{0.3}Co_{0.2}]O_2$ (NMC532) positive electrodes and graphite negative electrodes, were obtained sealed, without electrolyte, from LiFun Technologies (Xinma Industry Zone, Golden Dragon Road, Tianyuan District, Zhuzhou City, Hunan Province, PRC, 412000). The negative electrode of these cells was 96% artificial graphite particles (15-30 μm), 2% carbon black conductive diluent and 2% sodium carboxymethylcellulose (NaCMC)/styrene butadiene rubber (SBR) binder. The positive electrode was 96% NMC532 particles, 2% carbon black conductive diluent and 2% polyvinylidene fluoride (PVDF) binder. The ratio of negative/positive electrode capacity allowed for cell voltages of 4.5 V to be reached without lithium plating, delivering a capacity of 250 mAh. Prior to filling with electrolyte, the cells were opened and dried under vacuum for 14 hours at 100° C., to remove residual moisture. The cells were then transferred to an Argon-filled glovebox, without exposure to air. To each cell, 0.9 g of electrolyte was added. The electrolyte was prepared as described earlier in example 1. The aluminum-laminate cell casings were sealed at a temperature of 170° C., under a gauge pressure of −90 kPa, using a vacuum heat sealer (Model MSK-115A from MTI Corp).

After filling with electrolyte, the cells were held at 1.5 V for 24 hours. This allowed time for the electrolyte to permeate the electrodes. The voltage of 1.5 V was applied to prevent oxidation of the copper current collector, which occurs above 3.2 V vs $Li/Li^+$. Cells were then transferred to a 40.0±0.1° C. temperature-controlled box, and charged using a Maccor 4000 series test system. The charging procedure began with a C/20 charge to 3.5 V, followed by a one hour constant voltage hold at 3.5 V. During this step, EC and other electrolyte components are reduced, forming the negative electrode solid-electrolyte interphase (SEI) and causing gaseous by-products. The gas was removed from the cells which underwent the normal pouch cell formation procedure. For degassing, the cells were transferred to an Argon-filled glove box, where the cell casings were cut open to release the gas. The cells were then resealed under −90 kPa gauge pressure. The degassed cells were returned to the temperature-controlled box, where the charging procedure continued to 4.1, 4.3 or 4.5 V.

After degassing, the cells were placed in temperature-controlled boxes, maintained at 55° C., and cycled with a battery cycling system made by E-One Moli Energy Canada Ltd. A constant current of C/3 was used to charge/discharge the cells between 3.1 V and one of 4.1, 4.3, or 4.5 V depending on the voltage attained during the charging procedure. 200 cycles were obtained before the cells were removed from the charger for dissection and electrolyte analysis.

Cells were first discharged to 0.0 V, to prevent shorting. Cell tabs were then removed with scissors, and external markings on the cell were removed with acetone. The cell casings were cut along the top and bottom of the jelly rolls just before they were sealed in 15-mL polypropylene centrifuge vials. The vials were centrifuged at 2200 revolutions per minute (RPM), for 20 minutes, at 30° C. The cells were then immediately removed from the vials after centrifuging. The electrolyte extracted from the cells was removed from the vial using a 1 mL syringe.

For GC-MS, one drop of extracted electrolyte was added to a perfluoroalkoxy polymer vial containing 10 mL of dichloromethane (to extract the organics) and approximately 0.1 mL of pure water (18.2 MΩ cm, Barnstead Nanopure Diamond), to extract the $LiPF_6$. The vials were shaken twice in 15-minute intervals, then centrifuged at 2200 RPM, for 20 minutes, at 20° C. This procedure ensured that salts were adequately removed from the organic layer, as they are not suitable for GC-MS analysis. The organic (dichloromethane) layer was then transferred to a sample vial and placed on the auto sampler for GC-MS.

The samples were then analyzed on a Bruker 436 gas chromatograph (GC), coupled to a Bruker Scion single quadrupole mass spectrometer. The GC used a split injection with helium as the carrier gas, flowing at a rate of 1.3 mL/min. The column was 30 m long, with an internal diameter of 0.35 mm, and an internal coating 1 μm thick. The oven temperature ramped from 40° C. to 240° C., at a rate of 30° C./min to 240° C., to maximize peak quality and separation and to elute the heavier compounds. The mass spectrometry transfer line was held at 270° C., the ion source was set to 270° C., and the electron energy was set to 70 eV. After initial solvent elution, a total ion scan was performed to identify known and potentially unknown peaks. Knowns peaks were identified and quantified via retention time and ionic ratios. A minimum five-point calibration curve was used to determine the relative amounts of the compounds in each sample. Analytes included DMC, ethylmethyl carbonate (EMC), vinylene carbonate (VC), diethyl carbonate (DEC), FEC, EC, dimethyl-2,5-dioxahexane carboxylate (DMOHC) and diethyl-2,5-dioxahexane carboxylate (DEOHC).

Further, the concentrations of $LiPF_6$ and other electrolyte components were determined using ICP-OES technique. 0.10 g of each electrolyte was diluted twice into 15-mL centrifuge vials containing approximately 10.0 g of 2% $HNO_3$ to obtain a Li concentration in the measurable linear range. The vials were capped, and their lids were wrapped with Parafilm. Samples were analyzed on a Perkin Elmer Optima 8000 ICP-OES. A three-point calibration was prepared in 2% $HNO_3$, and measured before and after each sample set.

FIG. 9 compares the sensitivity, speed and cost of the FTIR/machine-learning method against other analytical tools that are commonly used for characterizing electrolyte in lithium-ion cells. FTIR/ML method has competitive accuracy, but is not sensitive to electrolyte additives and other trace components. However, it has several substantial advantages over other methods. The first advantage of the FTIR/ML method is speed of analysis. Only several seconds were needed to measure each FTIR spectrum. Only several milliseconds of computer time were needed to compare each FTIR spectrum with the existing spectral database of FTIR spectra using machine learning algorithm. Considerably more time and effort would be needed to characterize these electrolyte samples with other methods. GC-MS requires over one hour per sample, for sample preparation, data collection and analysis. Nuclear magnetic resonance (NMR) spectroscopy and ICP-OES also require several minutes for sample preparation, preparation of calibration solutions, and data analysis. The second advantage of FTIR/ML method is that it does not require sample preparation. Electrolyte can be analyzed neat, as opposed to other methods, where electrolyte must be diluted in harsh or expensive solutions. The third advantage of the FTIR/ML method is that it is able to quantify both the solvent and the salt concentrations simultaneously. It is expected that the accuracy and sensitivity of the FTIR/ML method is sufficient for the analysis of principle electrolyte components (>5% wt.) in aged lithium-ion cells, where large amounts of capacity fade are expected to cause changes in the electrolyte. The final advantage of the FTIR/machine learning method is cost. The FTIR spectrometer used in this work was purchased for around $18,000 USD, which is about an order of magnitude less than the cost of the other instruments as shown in FIG. 9.

Further, the machine-learning algorithms disclosed here to analyze electrolyte concentration can be applied using other spectrometers. The combination of the ML algorithms with other spectrometers, for example, the GC-MS, HPLC, ICP-OES, NMR, or another spectrometer or instrument, similarly allow for the rapid analysis of solutions and compounds, although the cost may be great, due to increased costs of the spectrometer. However, the specific algorithms may need to be altered, including providing different training data, specific to the spectrometer and system being analyzed.

Figures 10A, 10B:
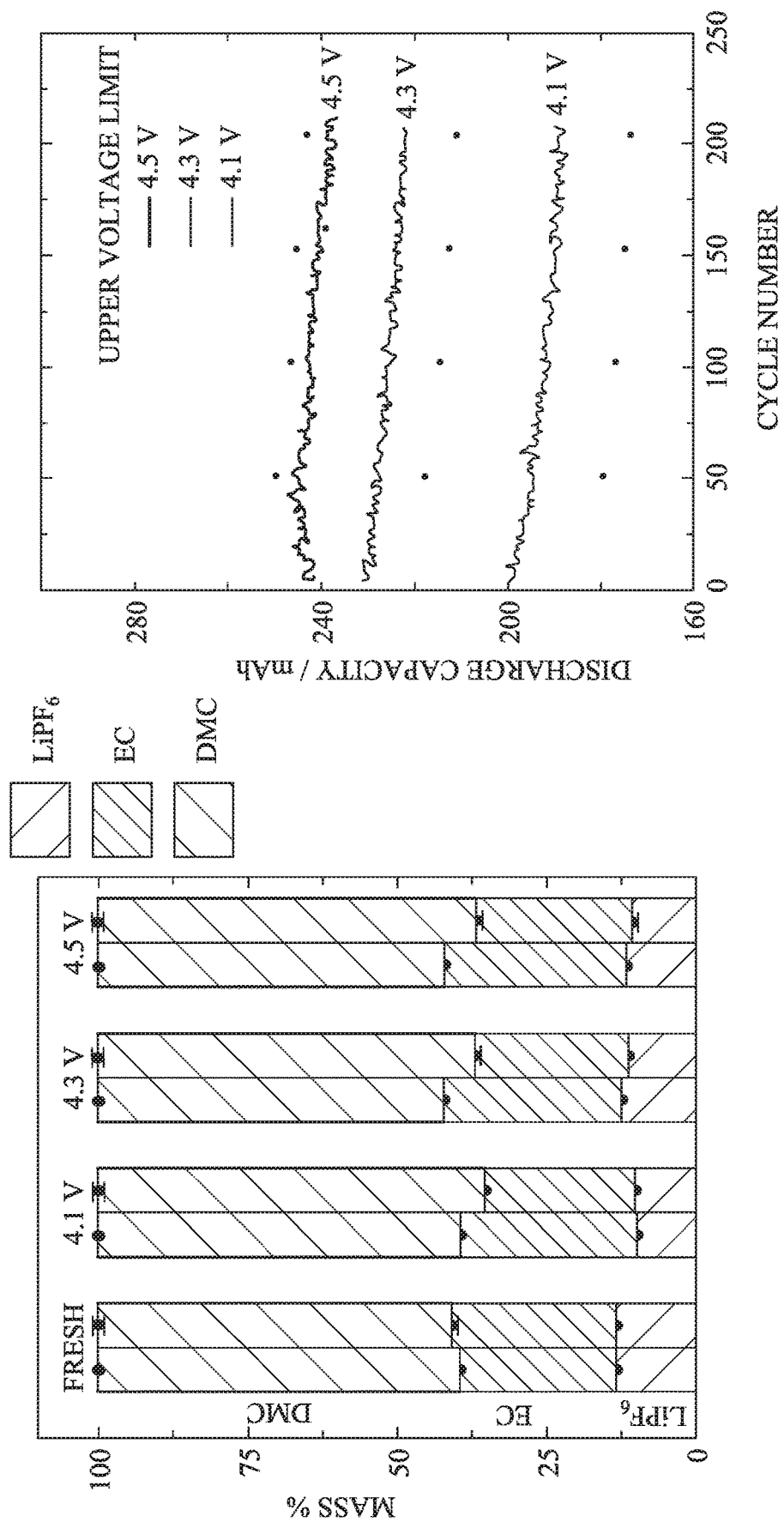
FIG. 10A illustrates the composition of electrolyte extracted from cycled cells, determined by GC-MS, ICP-OES, and FTIR/ML methods according to certain embodiments of the invention.
FIG. 10B illustrates capacity vs. cycle number for the cycled cells according to certain embodiments of the invention.

FIG. 10A compares the results of the FTIR/ML, GC-MS, and ICP-OES analyses on electrolyte sample extracted from aged lithium-ion cells. FIG. 10B shows capacity vs. cycle number for the cells, which were cycled at 55° C., at a rate of C/3, between 3.1 V and 4.1 (bottom curve), 4.3 (middle curve), or 4.5 V (top-most curve). These cells only exhibited a small amount of capacity fade and hence the expected changes to the electrolyte are small. The cells were filled with electrolyte which was prepared to contain $LiPF_6$, EC and DMC in a 14.3/25.7/60.0 weight ratio. The weight ratios of $LiPF_6$ (bottom portion in each result in FIG. 10A), EC (middle portion in each result in FIG. 10A), and DMC (top portion in each result in FIG. 10A) were measured using GC-MS and ICP-OES methods (left column for each cell) and FTIR/ML methods (right column for each cell). The weight ratios of $LiPF_6$, EC and DMC in the fresh electrolyte were found to be 13.1/26.5/60.4 by GC-MS and ICP-OES, and 13.3/27.5/59.3 by FTIR/ML. By GC-MS and ICP-OES methods, the weight ratios of $LiPF_6$, EC and DMC in electrolytes from cycled cells were found to be 9.8/29.5/60.7 for the cells cycled to 4.1 V, 12.5/29.8/57.8 for the cells cycled to 4.3 V, and 11.8/30/2/58.0 for the cells cycled to 4.5 V. By FTIR/ML method, the weight ratio of $LiPF_6$, EC and DMC in electrolytes from cycled cells were found to be 10.1/25.3/64.6 for the cells cycled to 4.1 V, 11.4/25.4/63.2 for the cells cycled to 4.3 V, and 10.5/26.3/63.3 for the cells cycled to 4.5 V.

FIG. 11 summarizes the results for the fresh electrolyte and for the electrolyte found in the cycled cells. Both ICP-OES and FTIR/ML methods show that 10-20% of the $LiPF_6$ in these cells was lost during cycling. This could be caused by the thermal decomposition of $LiPF_6$ at elevated temperature, and by the inclusion of $LiPF_6$ decomposition products in the thickening negative electrode SEI. The GC-MS and FTIR/ML methods do not come to the same result for the EC/DMC ratio. FIG. 12 shows the entire suite of species and their approximate relative amounts found by GC-MS method in the three cells. Some of the products found by GC-MS method originate from the decomposition of DMC and these cannot be detected by the FTIR/ML method.

The disclosure presents a new method for the characterization of liquid electrolyte solutions, using FTIR or another spectrometer and the machine learning algorithm. Experimental data exhibited good agreement between FTIR/ML, GC-MS, and ICP-OES methods on electrolytes taken from cycled Li-ion cells. It was found that the concentration of $LiPF_6$ was depleted by 10-20% in cells which had undergone 200 cycles at 55° C. This amount of salt loss is large, and is likely a significant contributor to eventual cell failure. The speed, ease and cost advantages of FTIR/ML or a spectrometer/ML will allow for analyses of the depletion of salt in aged lithium-ion cells and dramatic changes in solvent ratio. Using FTIR/ML or other spectrometer with the ML disclosed herein, it is now possible to easily and quickly analyze the electrolytes from all cells at the end of life or at some specified points during life. Further, analysis of the FTIR fingerprint region is now accessible within this analysis.

The foregoing disclosure is not intended to limit the present disclosure to the precise forms or particular fields of use disclosed. As such, it is contemplated that various alternate embodiments and/or modifications to the present disclosure, whether explicitly described or implied herein, are possible in light of the disclosure. Having thus described embodiments of the present disclosure, a person of ordinary skill in the art will recognize that changes may be made in form and detail without departing from the scope of the present disclosure. Thus, the present disclosure is limited only by the claims.

In the foregoing specification, the disclosure has been described with reference to specific embodiments. However, as one skilled in the art will appreciate, various embodiments disclosed herein can be modified or otherwise implemented in various other ways without departing from the spirit and scope of the disclosure. Accordingly, this description is to be considered as illustrative and is for the purpose of teaching those skilled in the art the manner of using various embodiments of the disclosed spectrometer/ML. It is to be understood that the forms of disclosure herein shown and described are to be taken as representative embodiments. Equivalent elements, materials, processes or steps may be substituted for those representatively illustrated and described herein. Moreover, certain features of the disclosure may be utilized independently of the use of other features, all as would be apparent to one skilled in the art after having the benefit of this description of the disclosure. Expressions such as "including", "comprising", "incorporating", "consisting of", "have", "is" used to describe and claim the present disclosure are intended to be construed in a non-exclusive manner, namely allowing for items, components or elements not explicitly described also to be present. Reference to the singular is also to be construed to relate to the plural.

Further, various embodiments disclosed herein are to be taken in the illustrative and explanatory sense, and should in no way be construed as limiting of the present disclosure. All joinder references (e.g., attached, affixed, coupled, connected, and the like) are only used to aid the reader's understanding of the present disclosure, and may not create limitations, particularly as to the position, orientation, or use of the systems and/or methods disclosed herein. Therefore, joinder references, if any, are to be construed broadly. Moreover, such joinder references do not necessarily infer that two elements are directly connected to each other.

Additionally, all numerical terms, such as, but not limited to, "first", "second", "third", "primary", "secondary", "main" or any other ordinary and/or numerical terms, should also be taken only as identifiers, to assist the reader's understanding of the various elements, embodiments, variations and/or modifications of the present disclosure, and may not create any limitations, particularly as to the order, or preference, of any element, embodiment, variation and/or modification relative to, or over, another element, embodiment, variation and/or modification.

It will also be appreciated that one or more of the elements depicted in the drawings/figures can also be implemented in a more separated or integrated manner, or even removed or rendered as inoperable in certain cases, as is useful in accordance with a particular application. Additionally, any signal hatches in the drawings/figures should be considered only as exemplary, and not limiting, unless otherwise specifically specified.

What is claimed is:

1. A computer-implemented method for determining a concentration of a component of an electrolyte, the computer-implemented method comprising:
   providing, to a spectrometer, instructions to capture a spectrum of a sample solution of the electrolyte and generate a signal representing the spectrum;
   receiving, from the spectrometer, the signal;
   analyzing the signal to determine one or more spectral features of the spectrum;
   preparing a database of spectra corresponding to solutions having predetermined concentrations of the component of the electrolyte, the database comprising a plurality for spectral features for each solution;
   determining a machine learning model using the database of spectra, the machine learning model based on at least one of the plurality of spectral features and the concentration of the component of the electrolyte; and
   determining the concentration of the component of the electrolyte in the sample solution using the machine learning model, wherein the component of the electrolyte is $LiPF_6$.

2. The computer-implemented method of claim 1, wherein the spectrometer is one of an infrared spectrometer, a Raman spectrometer, and an ultraviolet visible (UV-Vis) spectrometer.

3. The computer-implemented method of claim 2, wherein the spectrometer is a Fourier transform infrared (FTIR) spectrometer.

4. The computer-implemented method of claim 3, wherein providing instructions comprises providing instructions to the spectrometer to perform attenuated total reflectance (ATR) Fourier Transform infrared spectroscopy on the sample solution.

5. The computer-implemented method of claim 3, wherein providing instructions comprises providing instructions to the infrared spectrometer to capture the infrared spectrum of the sample solution using infrared radiation having a wavenumber between 500 $cm^{-1}$ to 1500 $cm^{-1}$.

6. The computer-implemented method of claim 3, wherein analyzing the signal to determine the one or more spectral features of the infrared spectrum comprises determining an area of the signal in a first set of predetermined regions.

7. The computer-implemented method of claim 3, wherein analyzing the signal to determine one or more spectral features of the infrared spectrum comprises determining a wavenumber of the signal in a second set of predetermined regions.

8. The computer-implemented method of claim 3, wherein determining the machine learning model comprises fitting the variation of each of the plurality of spectral features with the corresponding predetermined concentrations of the component of the electrolyte on a surface using least squares fitting technique.

9. The computer-implemented method of claim 8, wherein determining the concentration of the component of the electrolyte comprises fitting the one or more spectral features to the corresponding surface determined by the machine learning model.

10. A system for determining a concentration of a component of an electrolyte in a lithium-ion cell, the system comprising:
    a spectrometer configured to:
       subject a sample solution of the electrolyte to radiation;
       capture a spectrum of the sample solution of the electrolyte; and
       produce a signal representing the spectrum; and
    a processor in electrical communication with the spectrometer, the processor configured to:
       analyze the signal to determine one or more spectral features of the spectrum;
       prepare a database of spectra corresponding to solutions having predetermined concentrations of the component of the electrolyte, the database comprising a plurality for spectral features for each solution;
       determine a machine learning model using the database of spectra, the machine learning model based on at least one of the plurality of spectral features and the concentration of the component of the electrolyte; and
       determine the concentration of the component of the electrolyte in the sample solution using the machine learning model, wherein the component of the electrolyte is $LiPF_6$.

11. The system of claim 10, wherein the spectrometer is one of an infrared spectrometer, a Raman spectrometer, and an ultraviolet visible (UV-Vis) spectrometer.

12. The system of claim 11, wherein the spectrometer is a Fourier transform infrared (FTIR) spectrometer.

13. The system of claim 12, wherein the spectrometer is configured to subject the sample solution to infrared radiation having a wavenumber between 500 $cm^{-1}$ to 1500 $cm^{-1}$.

14. The system of claim 12, wherein the processor is configured to analyze the signal to determine the one or more spectral features of the infrared spectrum by determining an area of the signal in a first set of predetermined regions.

15. The system of claim 12, wherein the processor is configured to analyze the signal to determine the one or more spectral features of the infrared spectrum by determining a wavenumber of the signal in a second set of predetermined regions.

16. The system of claim 12, wherein the processor is configured to determine the machine learning model by fitting the variation of each of the plurality of spectral features with the corresponding predetermined concentrations of the component of the electrolyte on a surface using least squares fitting technique.

17. The system of claim 16, wherein the processor is configured to determine the concentration of the component of the electrolyte by fitting the one or more spectral features to the corresponding surface determined by the machine learning model.

18. The system of claim 17, wherein the processor is configured to determine the concentration of the component of the electrolyte by fitting the one or more spectral features using least squares fitting technique.

19. A computer-readable medium for use in conjunction with a spectrometer to determine a concentration of a component of an electrolyte, the computer-program product comprising a non-transitory computer-readable storage medium having instructions for causing a processor to:

provide, to the spectrometer, instructions to capture a spectrum of a sample solution of the electrolyte and generate a signal;

receive, from the spectrometer, the signal;

analyze the signal to determine one or more spectral features of the spectrum;

prepare a database of spectra corresponding to solutions having predetermined concentrations of the component of the electrolyte, the database comprising a plurality for spectral features for each solution;

determine a machine learning model using the database of spectra, the machine learning model based on at least one of the plurality of spectral features and the concentration of the component of the electrolyte; and determine the concentration of the component of the electrolyte in the sample solution using the machine learning model, wherein the component of the electrolyte is $LiPF_6$.

* * * * *